US00PP27201P2

(12) United States Plant Patent
Van Swieten

(10) Patent No.: US PP27,201 P2
(45) Date of Patent: Sep. 27, 2016

(54) *PHALAENOPSIS* ORCHID PLANT NAMED 'PHALDISXO'

(50) Latin Name: ***Phalaenopsis* hybrid**
Varietal Denomination: PHALDISXO

(71) Applicant: ANTHURA B.V., Bleiswijk (NL)

(72) Inventor: Martinus Nicolaas Gerardus Van Swieten, Leimuiden (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 14/545,662

(22) Filed: Jun. 3, 2015

(51) Int. Cl.
*A01H 5/02* (2006.01)

(52) U.S. Cl.
USPC ..... Plt./311

(58) Field of Classification Search
USPC ..... Plt./311
CPC ..... A01H 5/02
See application file for complete search history.

(56) References Cited

PUBLICATIONS

GTITM UPOVROM Citation for 'Phaldisxo' as per PBR QZ 20143355; Dec. 11, 2014; 1 page.*

* cited by examiner

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALDISXO', particularly characterized by having light purple dotted flowers, 1-3 peduncles, a peduncle that is long and moderate, leaves that are narrow obovate and very elongated, and is propagated by tissue culture is disclosed.

3 Drawing Sheets

Genus and species: *Phalaenopsis* hybrid.
Variety denomination: 'PHALDISXO'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALDISXO'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes or panicles, often with many showy flowers which open in succession beginning with the lowermost. The flowers possess three sepals and three petals; the lateral ones being alike. The lowermost petals, called the labellum, are three-lobed and are often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALDISXO' is particularly characterized by its attractive and unique light purple dotted flowers, economical propagation by tissue culture, rapid growth, and a plant dimension suitable for packaging and shipping to the market.

'PHALDISXO' is a product of a planned breeding program conducted by the inventor in Bleiswijk, The Netherlands.

The new *Phalaenopsis* 'PHALDISXO' originated from a cross made in June 2005 in Bleiswijk, The Netherlands. The female parent is a pink dotted *Phalaenopsis* pot plant named '12656-0002' (unpatented), while the male parent is a white *Phalaenopsis* pot plant named '06541-0001' (unpatented). A single plant was selected in June 2008 and has been asexually reproduced repeatedly by meristem tissue culture in Bleiswijk, The Netherlands over a 4-year period. The new variety has been found to retain its distinctive characteristics through successive asexual propagations.

Asexual reproduction of 'PHALDISXO' by tissue culture was first performed in July 2011 in Bleiswijk, The Netherlands and has demonstrated that the new cultivar is firmly fixed and retained through successive generations of asexual reproduction.

Plant Breeder's Rights for this variety have been applied for in Europe on Dec. 11, 2014. 'PHALDISXO' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Light purple dotted flowers;
2) 1-3 peduncles;
3) Peduncle is long and moderate;

4) The shape of the leaf is narrow obovate and very elongated; and
5) Plants are propagated by meristem tissue culture.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs are of a 50-week old plant grown in a greenhouse in Bleiswijk, The Netherlands in February 2015.

DESCRIPTION OF THE NEW VARIETY

Figure 1:
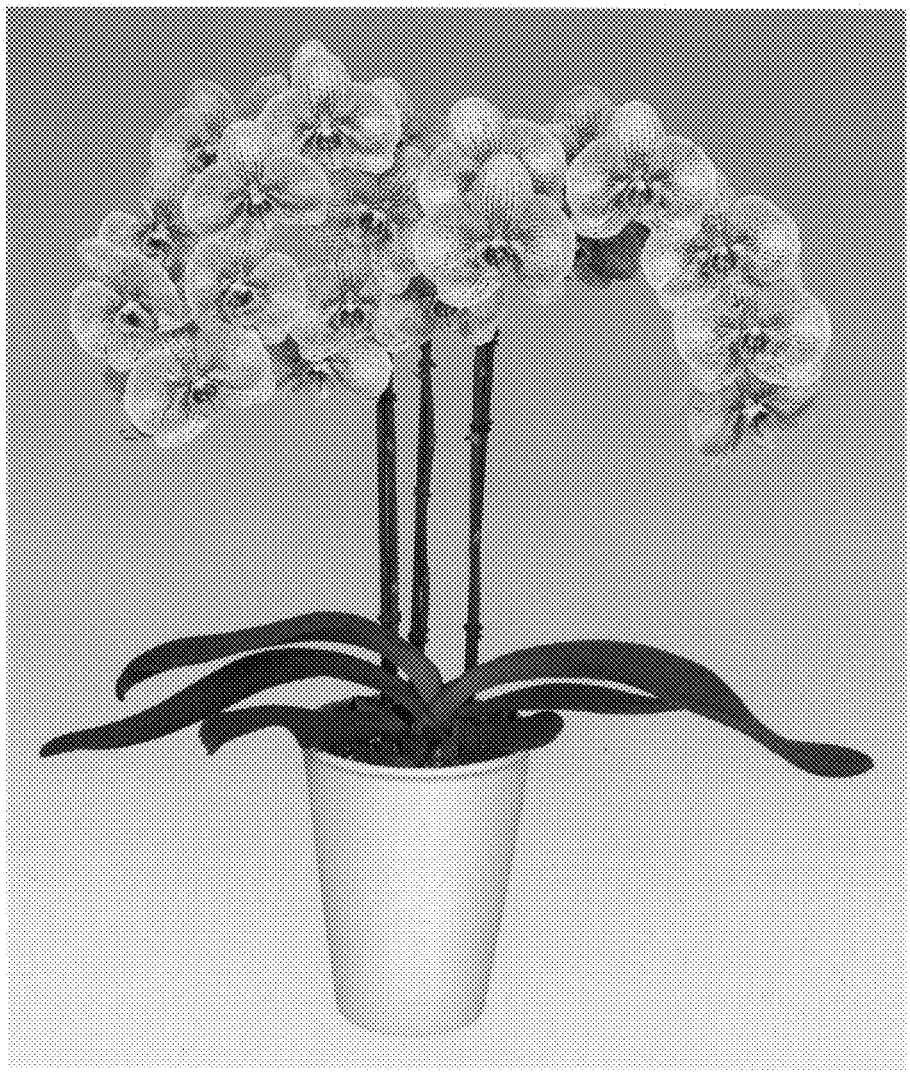
FIG. 1 shows the overall plant habit, including blooms and foliage of 'PHALDISXO'.
Figure 2:
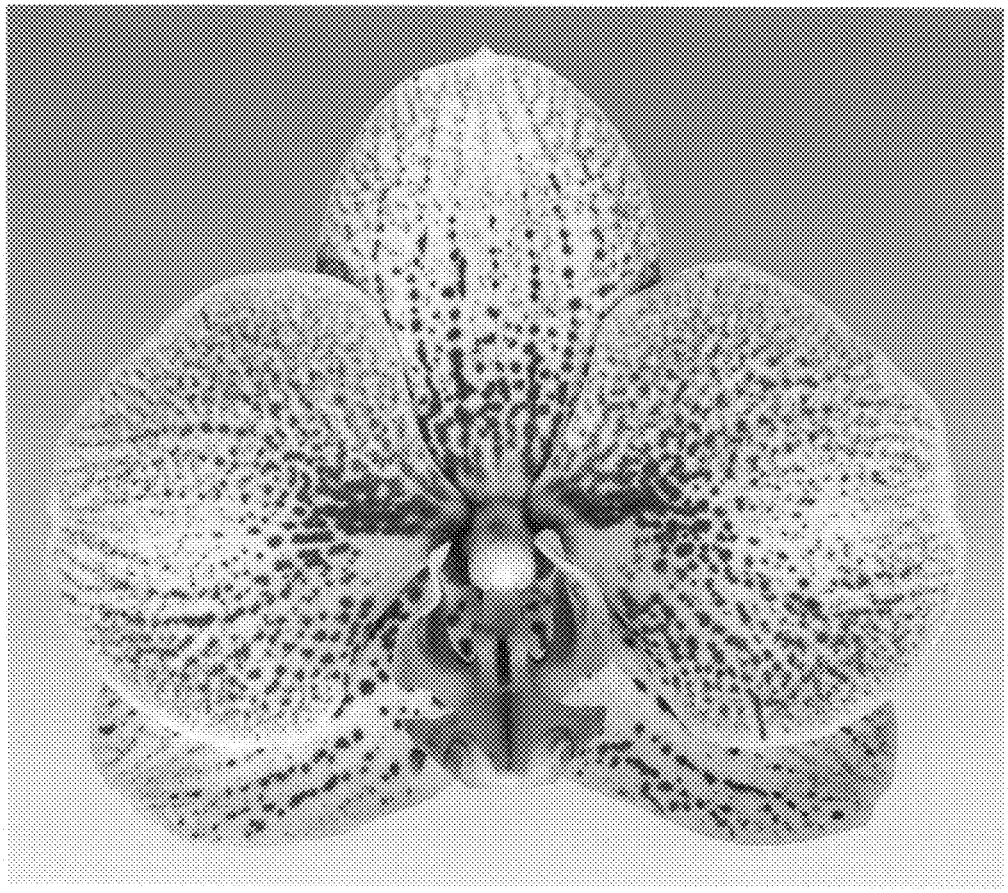
FIG. 2 shows a close-up of a flower of 'PHALDISXO'.
Figure 3:
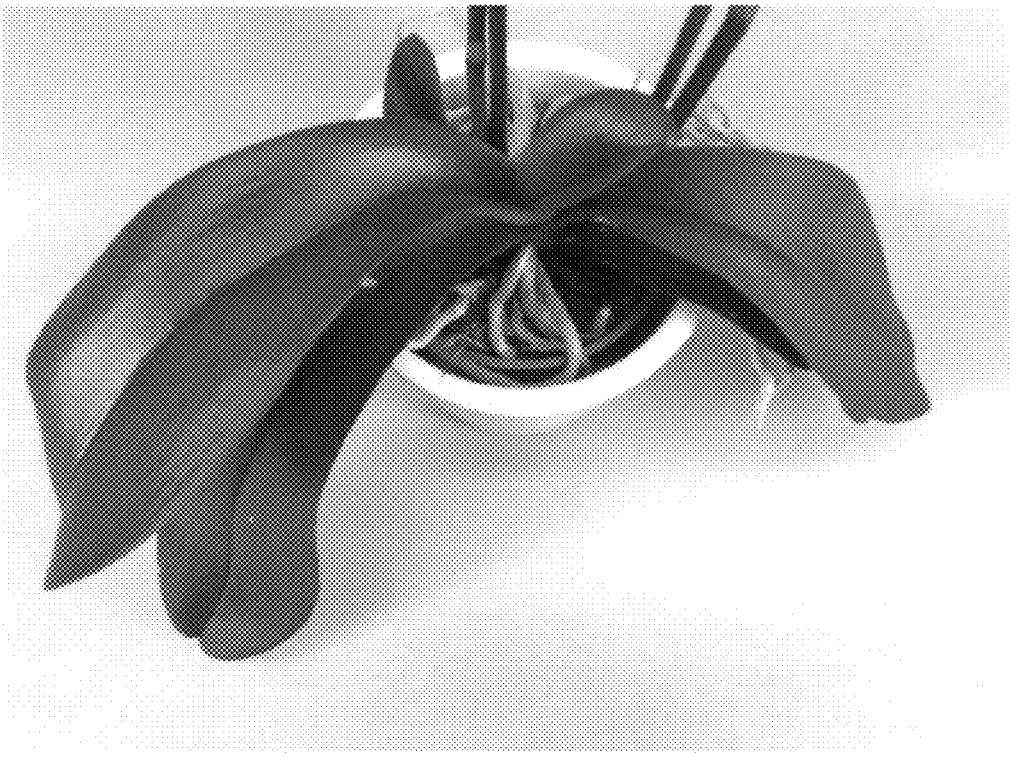
FIG. 3 shows a close-up of the leaves of 'PHALDISXO'.

The following detailed description sets forth the distinctive characteristics of 'PHALDISXO'. The data which define these characteristics were collected from asexual reproductions carried out in Bleiswijk, The Netherlands. The plant history was taken on 50-week old plants which were planted from a nursery tray in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in February 2015. Color readings were taken under 4-6000 lux natural light in the greenhouse. Color references are primarily to The R.H.S. Colour Chart of The Royal Horticultural Society of London (R.H.S.) (2001).

DETAILED BOTANICAL DESCRIPTION

Classification:
- *Family*.—Orchidaceae.
- *Botanical*.—*Phalaenopsis* hybrid.
- *Common name*.—*Phalaenopsis*.
- *Variety name*.—'PHALDISXO'.

Parentage:
- *Female parent*.—*Phalaenopsis* cultivar '12656-0002' (unpatented).
- *Male parent*.—*Phalaenopsis* cultivar '06541-0001' (unpatented).

Propagation:
- *Type*.—Tissue culture.

Plant:
- *Crop time* (*time to produce a finished flowering plant*).—48 to 50 weeks for a 12 cm pot.
- *Growth habit of peduncle*.—Standard, green leaves, panicle.
- *Height* (*including pot, including inflorescence*).—50.0 cm to 60.0 cm.
- *Width* (*measured from leaf tips*).—43.0 cm to 48.0 cm.
- *Vigor*.—Strong.

Roots:
- *Root description*.—Grey-green-colored roots with branching lateral roots having grey-green colored root tips.

Leaves:
- *Mature leaves*.—Quantity per plant: 7 to 9 leaves are produced before flowering. Length (fully expanded): 19.0 cm to 24.0 cm. Width: 7.0 cm to 8.0 cm. Shape: Narrow obovate. Base shape: Very elongated. Apex: Unequal mucronate. Leaf blade angle with the petiole: Between 10 degrees and 25 degrees (measured from petiole to leaf). Leaf margin: Entire.
- *Color*.—Upper surface: RHS 147A. Lower surface: RHS 146A.
- *Texture*.—Slightly rough.
- *Thickness*.—2.5 mm to 2.9 mm.
- *Venation*.—Pattern: Parallel. Color of the midvein: Upper surface: RHS 147A. Lower surface: RHS 146A.

Peduncle:
- *Quantity per plant*.—1-3.
- *Number of flowers per peduncle*.—8 to 16.
- *Length*.—42.0 cm to 47.0 cm.
- *Diameter*.—5.1 mm to 5.9 mm.
- *Strength*.—Moderate.
- *Aspect*.—Slightly pendant.
- *Texture*.—Smooth.
- *Color*.—Green-dark purple (RHS 146A and 187A).
- *Internode length*.—30.0 mm to 40.0 mm.
- *Callosities*.—None.

Inflorescence description:
- *Appearance*.—Upright to slightly pendant, panicle inflorescence with bilaterally symmetrical flowers that open in succession beginning with the lowermost flower.
- *Inflorescence size*.—Height (from base to tip): 180.0 mm to 220.0 mm. Diameter: 3.9 mm to 4.2 mm.
- *Flowering time*.—First flowers can be expected 10 to 11 months after planting in a 12 cm pot.
- *Flower*.—Height: 74.0 mm to 79.0 mm. Diameter: 75.0 mm to 85.0 mm. Depth of lip: 16.0 mm to 19.0 mm.
- *Flower longevity*.—On the plant: 17 to 19 weeks.
- *Fragrance*.—Absent.
- *Petals*.—Arrangement: Free. Shape: Semi-circular. Apex: Emarginated asymmetric. Margin: Slightly undulated. Length (from base to tip): 34.0 mm to 39.0 mm. Width: 42.0 mm to 47.0 mm. Color (when fully opened): Main color: Light purple (RHS 78C) dotted (RHS 71A, 78A). Note: Intensity of dots depends on the temperature: in lower temperatures the intensity is higher and in higher temperatures the intensity of dots is lower. At the base: Light purple (RHS 78C).
- *Dorsal sepal*.—Shape: Broad elliptic. Margin: Entire. Length (from base to tip): 38.0 mm to 43.0 mm. Width: 31.0 mm to 36.0 mm. Color (when fully opened): Main color: Light purple (RHS 78D) dotted (RHS 71A, 78A). At the base: Light purple (RHS 78D).
- *Lateral sepals*.—Shape: Ovate. Margin: Entire. Length (from base to tip): 35.0 mm to 40.0 mm. Width: 27.0 mm to 32.0 mm. Color (when fully opened): Main color: Light purple (RHS 78D) dotted (RHS 71A, 78A). At the base: Light purple (RHS 78D).
- *Labellum* (*lip*).—Margin: Entire. Length: 18.0 mm to 20.0 mm. Width: 16.0 mm to 18.0 mm. Whiskers: Present. Length of whiskers: Medium.
- *Lateral lobe*.—Shape: Type V (as described in the International Union for the Protection of New Varieties of Plants (UPOV) Test Guidelines for *Phalaenopsis*). Color: White (RHS 155C), yellow (RHS 7A), and purple (RHS 71A, 78A).
- *Apical lobe*.—Shape: Trullate. Color: White/light purple (RHS 155C, 80C), yellow/green toward the callus (RHS 7A, 1B).

*Callus*.—Color: Yellow/green (RHS 7A, 2B) with dark purple flecks (RHS 183A).

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 11.0 mm to 13.0 mm. Diameter: 4.7 mm to 5.6 mm. Color: White (RHS 155C) and light purple shaded (RHS 78A, 78B).

*Pollinia*.—Quantity: 2. Size: 1.3 mm to 1.5 mm. Color: Orange (RHS 26A).

*Ovary*.—Length: 8.0 mm to 10.0 mm. Diameter: 2.5 mm to 2.7 mm.

*Pedicel*.—Length: 32.0 mm to 35.0 mm. Diameter: 2.8 mm to 3.0 mm.

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALDISXO' differs from female parent '12656-0002' (unpatented) in that 'PHALDISXO' has flowers with a pink/purple dotted center and medium-sized whiskers, whereas '12656-0002' has flowers with a white flecked center and short whiskers. Additionally, 'PHALDISXO' has an apical lobe that is white/light purple and yellow/green towards the callus, whereas '12656-0002' has an apical lobe that is red-purple.

'PHALDISXO' differs from male parent '06541-0001' (unpatented) in that 'PHALDISXO' has a smaller flower that is lightly dotted, whereas '06541-0001' has a larger flower that is white and even. Additionally, 'PHALDISXO' has medium-sized whiskers, whereas '06541-0001' has long whiskers.

'PHALDISXO' differs from commercial variety 'PHALDESXEN' (unpatented) in that 'PHALDISXO' has flowers that are lighter colored with wider petals, whereas 'PHALDESXEN' has flowers that are darker colored with more narrow petals. Additionally, 'PHALDESXEN' has an apical lobe that is white/light purple and yellow/green toward the callus, whereas 'PHALDESXEN' has an apical lobe that is red-purple.

I claim:

1. A new and distinct variety of *Phalaenopsis* plant named 'PHALDISXO', substantially as described and illustrated herein.

* * * * *